US008411874B2

(12) United States Patent
Leichter

(10) Patent No.: US 8,411,874 B2
(45) Date of Patent: Apr. 2, 2013

(54) REMOVING NOISE FROM AUDIO

(75) Inventor: Jerrold Leichter, Stamford, CT (US)

(73) Assignee: Google Inc., Mountain View, CA (US)

(*) Notice: Subject to any disclaimer, the term of this patent is extended or adjusted under 35 U.S.C. 154(b) by 324 days.

(21) Appl. No.: 12/827,487

(22) Filed: Jun. 30, 2010

(65) Prior Publication Data

US 2012/0002820 A1 Jan. 5, 2012

(51) Int. Cl.

| | |
|---|---|
| ***H04R 29/00*** | (2006.01) |
| ***A61F 11/06*** | (2006.01) |
| ***G10K 11/16*** | (2006.01) |
| ***H03B 29/00*** | (2006.01) |

(52) U.S. Cl. ........ 381/71.8; 381/56; 381/71.1; 381/71.9

(58) Field of Classification Search ................. 381/73.1, 381/94.1, 71.1, 71.2, 56, 71.8, 71.9, 71.14

See application file for complete search history.

(56) References Cited

U.S. PATENT DOCUMENTS

| | | | | |
|---|---|---|---|---|
| 5,848,163 | A | 12/1998 | Gopalakrishnan et al. | |
| 5,930,372 | A | 7/1999 | Kuriyama | |
| 6,324,499 | B1 | 11/2001 | Lewis et al. | |
| 6,556,968 | B1 | 4/2003 | Shiono | |
| 6,935,797 | B2 | 8/2005 | Sim | |
| 7,433,484 | B2 | 10/2008 | Asseily et al. | |
| 7,519,186 | B2 * | 4/2009 | Varma et al. | 381/94.7 |
| 2003/0091182 | A1 | 5/2003 | Marchok et al. | |
| 2006/0018459 | A1 | 1/2006 | McCree | |
| 2006/0050895 | A1 | 3/2006 | Nemoto et al. | |
| 2006/0217973 | A1 | 9/2006 | Gao et al. | |
| 2007/0286347 | A1 | 12/2007 | Moore | |
| 2008/0118082 | A1 | 5/2008 | Seltzer et al. | |
| 2009/0010456 | A1 | 1/2009 | Goldstein et al. | |
| 2010/0062719 | A1 | 3/2010 | Diethorn | |
| 2012/0014514 | A1 | 1/2012 | Enbom et al. | |

FOREIGN PATENT DOCUMENTS

| | | |
|---|---|---|
| EP | 2 405 634 | 7/2010 |
| WO | 2012/006535 | 1/2012 |

OTHER PUBLICATIONS

International Search Report & Written Opinion for Application No. PCT/US2011/040679, dated Jul. 28, 2011, 12 pages.
European Search Report for Application No. EP10169088.1-1237, dated Jul. 12, 2010, 7 pages.
International Search Report & Written Opinion for Application No. PCT/US2011/043379, dated Nov. 2, 2011, 9 pages.

* cited by examiner

*Primary Examiner* — Vivian Chin
*Assistant Examiner* — Douglas Suthers
(74) *Attorney, Agent, or Firm* — Fish & Richardson P.C.

(57) ABSTRACT

The subject matter of this specification can be embodied in, among other things, a computer-implemented method for removing noise from audio that includes building a sound model that represents noises which result from activations of input controls of a computer device. The method further includes receiving an audio signal produced from a microphone substantially near the computer device. The method further includes identifying, without using the microphone, an activation of at least one input control from among the input controls. The method further includes associating a portion of the audio signal as corresponding to the identified activation. The method further includes applying, from the audio model, a representation of a noise for the identified activation to the associated portion of the audio signal so as to cancel at least part of the noise from the audio signal.

32 Claims, 4 Drawing Sheets

REMOVING NOISE FROM AUDIO

TECHNICAL FIELD

This document relates to removing noise from audio.

BACKGROUND

Teleconferences and video conferences are becoming ever more popular mechanisms for communicating. Many portable computer devices, such as laptops, netbooks, and smartphones, today have built-in microphones. In addition, many portable computer devices have built-in cameras (or can easily have an inexpensive external camera, such as a web cam, added). This allows for very low cost participation in teleconferences and video conferences.

It is common for participants in a conference to be typing during the conference. For example, a participant may be taking notes about the conference or multi-tasking while talking or while listening to others talk. With the physical proximity of the keyboard on the portable computer device to a microphone that may also be on the portable computer device, the microphone can easily pick up noise from the keystrokes and transmit the noise to the conference, annoying the other participants.

In headphones, it is common to remove unwanted ambient noise by building a model of the noise, and inserting the "inverse" of that noise in the audio signal to cancel the noise. The trick is to build a model that accurately matches the noise so that it can be removed without removing meaningful parts of the audio signal. For example, noise canceling headphones have small microphones outside the headphones themselves. Any sounds the headphones detect as coming from "outside" are potentially noise that should be canceled.

SUMMARY

In general, this document describes systems and methods for removing noise from audio. In certain examples, the actuation of keys on a computer device can be sensed separately by electrical contact being made within the key mechanisms and by sounds (e.g., clicking) of the keys received on a microphone that is electronically connected to the computer device. Such received data may be correlated, such as by aligning the two sets of data in time so as to identify the portion of the sounds received by the microphone that is attributable to the actuation of the keys, so that such portion may be selectively and partially or substantially removed from the sound. Previous actuation of the keys and associated sounds of such actuation may also be acquired under previous controlled conditions so that a model can more readily identify the part of a sound signal that can be attributed to the action of the keys, once the timing of the keys has been determined in the audio signal. The subsequent filtered signal can then be broadcast to other electronic devices such as to users of telephones or other computer devices that are on a conference call with a user of the computer device.

In one aspect, a computer-implemented method for removing noise from audio includes building a sound model that represents noises which result from activations of input controls of a computer device. The method further includes receiving an audio signal produced from a microphone substantially near the computer device. The method further includes identifying, without using the microphone, an activation of at least one input control from among the input controls. The method further includes associating a portion of the audio signal as corresponding to the identified activation. The method further includes applying, from the audio model, a representation of a noise for the identified activation to the associated portion of the audio signal so as to cancel at least part of the noise from the audio signal.

Implementations can include any, all, or none of the following features. The microphone is mounted to the computer device. The input controls include keys on a keyboard, the activations include physical actuations of the keys on the keyboard, and identifying the activation includes receiving a software event for the activation. The noises include audible sounds that result from the physical actuations of the keys. The model defines the audible sounds of the physical actuations of the keys by frequency and duration. Building the model includes obtaining, through the microphone, the audible sounds of the physical actuations of the keys. Obtaining the audible sounds of the physical actuations of the keys occurs as a background operation for training the computer device while one or more other operations are performed that use the keys. Building the model includes receiving the obtained audible sounds of the physical actuations of the keys at a server system that is remote from the computer device. The method includes receiving the audio signal and data representing timing of the activation of the key on the computer device at the server system. The noise includes electrical noise. The method includes sending the audio signal with the part of the noise removed over a network for receipt by participants in a teleconference. Associating the portion of the audio signal as corresponding to the identified activation includes correlating timing of receiving the portion and of receiving the activation. The method includes automatically calibrating the computer device to determine an amount of time between receiving the portion and receiving the activation.

In one aspect, a computer program product, encoded on a computer-readable medium, operable to cause one or more processors to perform operations for removing noise from audio includes building a sound model that represents noises which result from activations of input controls of a computer device. The operations further include receiving an audio signal produced from a microphone substantially near the computer device. The operations further include identifying, without using the microphone, an activation of at least one input control from among the input controls. The operations further include associating a portion of the audio signal as corresponding to the identified activation. The operations further include applying, from the audio model, a representation of a noise for the identified activation to the associated portion of the audio signal so as to cancel at least part of the noise from the audio signal.

Implementations can include any, all, or none of the following features. The microphone is mounted to the computer device. The input controls include keys on a keyboard, the activations include physical actuations of the keys on the keyboard, and identifying the activation includes receiving a software event for the activation. The noises include audible sounds that result from the physical actuations of the keys. The model defines the audible sounds of the physical actuations of the keys by frequency and duration. Building the model includes obtaining, through the microphone, the audible sounds of the physical actuations of the keys. Obtaining the audible sounds of the physical actuations of the keys occurs as a background operation for training the computer device while one or more other operations are performed that use the keys. Building the model includes receiving the obtained audible sounds of the physical actuations of the keys at a server system that is remote from the computer device. The operations include receiving the audio signal and data representing timing of the activation of the key on the computer device at the server system. The noise includes electrical noise. The operations include sending the audio signal with the part of the noise removed over a network for receipt by participants in a teleconference. Associating the portion of the audio signal as corresponding to the identified activation includes correlating timing of receiving the portion and of receiving the activation. The operations include automatically calibrating the computer device to determine an amount of time between receiving the portion and receiving the activation.

In one aspect, a computer-implemented system for removing noise during a teleconference includes a sound model generated to define noises which result from input controls being activated on a computer device. The system further includes an interface to receive first data that reflects electrical activation of the input controls and second data that reflects an audio signal received by a microphone in communication with the computer device. At least a portion of the audio signal includes one or more of the noises which result from activation of the input controls on the computer device. The system further includes a noise cancellation module programmed to correlate the first data with the second data and to use representations of the one or more noises from the sound model to cancel the one or more noises from the portion of the audio signal received from the microphone.

Implementations can include any, all, or none of the following features. The microphone is mounted to the computer device. The input controls include keys on a keyboard of the computer device and activation of the input controls includes physical actuation of the keys on the keyboard.

The systems and techniques described here may provide one or more of the following advantages. First, a system can allow a user to interact with one or more input controls, such as a keyboard or button, while speaking into a microphone without distracting an audience that listens to the recording with the sounds of those input controls. Second, a system can provide a software solution for reducing noise from input controls, such as a keyboard or button, during a recording on a computer device. Third, a system can reduce noise from input controls during a recording on a computer device without the addition of further hardware to the computer device, such as additional microphones. Fourth, a system can provide for canceling noise at a central server system and distributing the noise canceled audio to multiple computer devices.

The details of one or more implementations are set forth in the accompanying drawings and the description below. Other features and advantages will be apparent from the description and drawings, and from the claims.

DETAILED DESCRIPTION

This document describes systems and techniques for removing noise from audio. In general, audio input to a computing device may be modified, such as to filter or cancel noise that results from one or more other input devices being used. For example, the noise may be the sounds of key presses, button clicks, or mouse pad taps and the sounds can be removed from the audio that has been captured. In another example, the noise may be electromagnetic noise, such as electromagnetic interference with the audio input caused by another input device. With the noise from the input devices removed, the audio can then be recorded and/or transmitted. This removal may occur, for example, prior to the audio being sent from the computing device to another computing device that is participating in a teleconference or videoconference. In another example, the raw audio can be provided to an intermediate system where the noise is filtered or canceled and then provided to another computing device.

Figure 1:
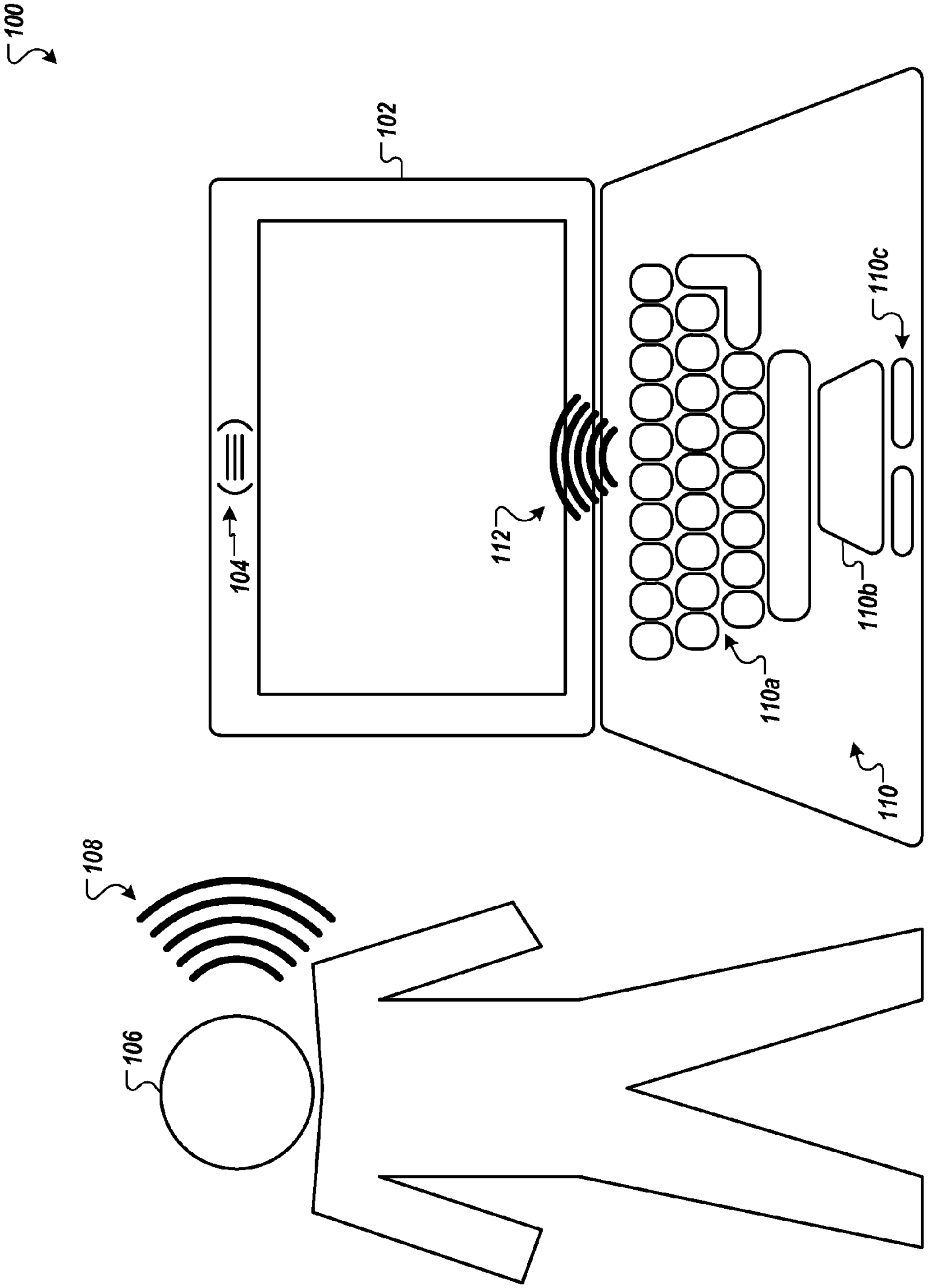
FIG. 1 is a schematic diagram that shows an example of a system for removing noise from audio.

FIG. 1 is a schematic diagram that shows an example of a system 100 for removing noise from audio. The system 100 generally includes a computing device 102 equipped with a microphone 104. The system 100 can access software for correlating activation events from one or more input devices on the computing device 102 with noise that results from the activation events. Activation events and input devices can include, for example, key presses on a keyboard, clicks on a button, scrolling of a trackball or mouse wheel, or taps on a touch pad. The noise, in the case of audible noise, is included in or, in the case of electromagnetic noise, interferes with an audio signal received via the microphone 104. The system 100 can identify the relationship between such received data in order to better filter out the noise of the activation events from audio captured via the microphone 104.

As noted, the computing device 102 receives audio input via the microphone 104. The audio input includes both intended audio, such as a speech input 108 from a user 106, and unintended audio or interference, such as one or more noises 112 that result from activating one or more input controls 110. The input controls can include, for example, keys in a keyboard 110*a*, a touchpad 110*b*, and other keys in the form of one or more buttons 110*c*. In some implementations, the input controls 110 can include a touchscreen, scroll wheel, or a trackball. The computing device 102 uses active noise control processes to filter the audio input to isolate the speech input 108 of the user 106, or other audio, from the noises 112 produced by the input controls 110.

In using the computing device 102, the user 106 may speak while making one or more inputs with the input controls 110. Activating the input controls 110 produces the noises 112. The noises 112 combine with the speech input 108, and the combined sounds are received by the microphone 104 and/or the computing device 102 as audio input. The computing device 102 modifies the audio input to cancel or filter the noises 112, leaving only, or substantially only, the speech input 108 from the user 106, or at least the non-noise content of the audio. Substantially can include, for example, a significant or noticeable reduction in the magnitude of the noises 112 as compared to the speech input 108. The modified audio input can be sent, for example, to one or more remote computing devices that are participating in a teleconference. The remote computing devices can then play back the modified audio to their respective users.

The computing device 102, which in this example is a laptop computer, executes one or more applications that receive audio input from the microphone 104 and concurrently receive another input, such as electronic signals indicating the actuation of a key press on the keyboard 110*a*, a selection of the buttons 110*c*, or a tap on the touchpad 110*b*. The computing device 102 also stores representations of the sound produced by the key press, button click, and other input events. For example, the representations may be stored as waveforms. When the computing device 102 receives a particular input event, such as by recognizing that the contacts on a particular key or button have been connected or a key press event being raised by an operating system of the computing device 102, the computing device 102 retrieves the associated representation and applies the representation to the recorded audio from the microphone 104 to cancel the sound produced by the input event.

In some implementations, the applications that receive the audio input can include a teleconferencing or remote education application. The teleconferencing or remote education application may provide the modified recorded audio to one or more remote computing devices that are participating in the teleconference or remote education session. The recorded audio may be stored for a definite period of time in certain applications, and may also be streamed, transmitted, and not subsequently stored.

Alternatively, the teleconferencing or remote education application may provide audio data to an intermediate system, such as a teleconferencing server system. For example, the computing device 102 can provide the modified audio to the teleconferencing server system. In another example, the computing device 102 can provide the unmodified audio data and data describing the input control activation events (e.g., key contacts being registered by the computing device 102, apart from what sound is heard by the microphone 104), such as an identification of the specific events and times that the specific events occurred relative to the audio data. The teleconferencing server system can then perform the noise cancellation operations on the audio data. For example, the teleconferencing server system may have previously stored, or may otherwise have access to, the representations of the sounds produced by activating the input controls 110 (or input controls on a similar form of device, such as a particular brand and model of laptop computer). The teleconferencing server system uses the event identifications and the timing information to select corresponding ones of the representations and to apply those representations at the correct time to cancel the noise from the audio data. The teleconferencing server system can then provide the modified audio to the remote computing devices.

In some implementations, the microphone is substantially near the computing device 102. Substantially near can include the microphone 104 being mounted to the computing device 102 or placed a short distance from the computing device 102. For example, as shown in FIG. 1, the microphone 104 is integrated within a housing for a laptop type of computing device. In another example, a microphone that is external to the computing device 102 can be used for receiving the audio input, such as a freestanding microphone on the same desk or surface as the computing device 102 or a headset/earpiece on a person operating the computing device 102. In another example, the microphone 104 can be placed on the computing device 102, such as a microphone that rests on, is clipped to, or is adhered to a housing of the computing device 102. In yet another example, the microphone 104 can be located a short distance from the computing device 102, such as several inches or a few feet. In another example, the microphone 104 can be at a distance and/or a type of contact with the computing device 102 which allows vibration resulting from activation of input controls to conduct through a solid or semi-solid material to the computing device 102.

In some implementations, the computing device 102 can be a type of computing device other than a laptop computer. For example, the computing device 102 can be another type of portable computing device, such as a netbook, a smartphone, or a tablet computing device. In another example, the computing device 102 can be a desktop type computing device. In yet another example, the computing device 102 can be integrated with another device or system, such as within a vehicle navigation or entertainment system.

In certain implementations more or less of the operations described here can be performed on the computing device 102 versus on a remote server system. At one end, the training of a sound model to recognize the sounds of key presses, and the canceling or other filtering of the sounds of key presses may all be performed on the computing device 102. At the other end of the spectrum, the processing and filtering may occur on the server system, with the computing device 102 simply sending audio data captured by the microphone 104 along with corresponding data that is not from the microphone 104 but directly represents actual actuation of keys on the computing device 102. The server system in such an implementation may then handle the building of a sound model that represents the sounds made by key presses, and may also subsequently apply that model to sounds passed by the computing device 102, so as to remove in substantial part sounds that are attributable to key presses.

Figure 2:
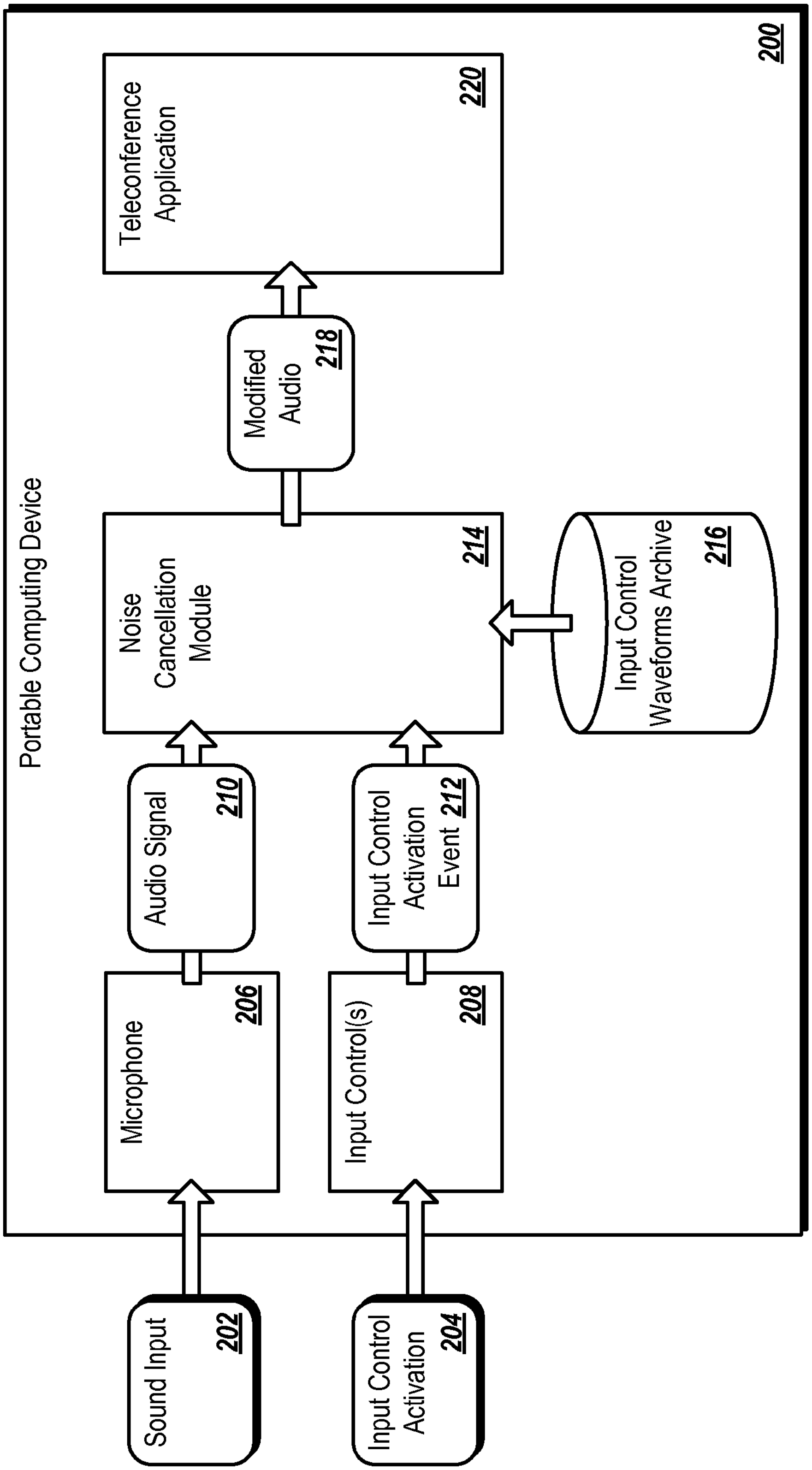
FIG. 2 is a block diagram that shows an example of a portable computing device for removing noise from audio.

FIG. 2 is a block diagram that shows an example of a portable computing device 200 for removing noise from audio. The portable computing device 200 may be used, for example, by a presenter of a teleconference. The presenter's speech can be broadcast to other client computing devices while the presenter uses a keyboard or other input control during the teleconference. The portable computing device 200 cancels or reduces the sound of key presses and other background noises that result from activating the input controls, in order to isolate the speech or other audio that is intended to be included in the audio signal, from the noises that result from activation of the input controls.

The portable computing device 200 includes a microphone 206 for capturing a sound input 202. The microphone 206 can be integrated into the portable computing device 200, as shown here, or can be a peripheral device such as a podium microphone or a headset microphone. The portable computing device 200 includes at least one input control 208, such as a keyboard, a mouse, a touch screen, or remote control, which receives an activation 204, such as a key press, button click, or touch screen tap. An activation of a key is identified by data received from the key itself (e.g., electrical signal from contact being made in the key and/or a subsequent corresponding key press event being issued by hardware, software, and/or firmware that processes the electrical signal from the contact) rather than from sounds received from the microphone 206, through which activation can only be inferred.

The input control 208 generates an activation event 212 that is processed by one or more applications that execute on the portable computing device 200. For example, a key press activation event may result in the generation of a text character on a display screen by a word processor application, or a button click (another form of key press) activation event may be processed as a selection in a menu of an application. In addition to creating the activation event 212, the activation 204 of the input control 208 also results, substantially simultaneously as perceived by a typical user, in the generation of an audible sound or noise. In some instances, the audible sound is an unintended consequence of activating mechanical parts of the input control 208 and/or from the user contacting the input control 208, such as a click, a vibration, or a tapping sound. In the example of a microphone integrated within the portable computing device 200, this unintended noise can appear magnified when registered by the microphone 206. This may be a result of the key actuation vibrating the housing of the portable computing device 200 and the housing transferring that vibration to the microphone 206.

The microphone 206 creates an audio signal 210 from the sound input 202 and passes the audio signal 210 to a noise cancellation module 214. The input control 208 causes the generation of the activation event 212 as a result of the activation 204 of the input control 208 and passes data that indicates the occurrence of the activation event 212 to the noise cancellation module 214. In some implementations, the noise cancellation module 214 is a software module or program that executes in the foreground or background in the portable computing device 200. In some implementations, the audio signal 210 and/or data for the activation event 212 are routed by an operating system and/or device drivers of the portable computing device 200 from the microphone 206 and the input control 208 to the noise cancellation module 214.

The noise cancellation module 214 determines that the audio signal 210 contains the sound that results from the activation 204 of the input control 208 based upon the activation event 212. Such a determination may be made by correlating the occurrence of the activation event 212 with a particular sound signature in the audio signal 210, and then canceling the sound signature using stored information. For example, the noise cancellation module 214 can retrieve a representation of the sound, such as a waveform, from an input control waveform storage 216. The input control waveform storage 216 stores waveforms that represent the sounds produced by activation of the input controls in the portable computing device 200. The noise cancellation module 214 applies the waveform associated with the activation event 212 to the audio signal 210 to destructively interfere with the sound of the activation 204 to create a modified audio signal 218.

An input control waveform can be an audio signal substantially in phase, substantially in antiphase (e.g., 180 degrees out of phase), or substantially in phase and with an inverse polarity, with the sound input 202. In some implementations, such a waveform may also be constructed in real-time. In the case of a substantially in phase input control waveform, the inverse of the input control waveform can be added to the audio signal 210 to destructively interfere with the sound of the activation 204 and thus filter out such noise. In the case of an input control waveform substantially in antiphase or substantially in phase and with an inverse polarity with the sound input 202, the input control waveform can be added to the audio signal 210.

In some implementations, the input control waveforms can be created by the noise cancellation module 214 and stored in the input control waveform storage 216. For example, during a training session, the noise cancellation module 214 can use the microphone 206 to record one or more instances of the sound that results from the activation 204 of the input control 208. In the case of multiple instances, the noise cancellation module 214 may calculate an aggregate or an average of the recorded sounds made by activation of the input control 208. In some implementations, the manufacturer of the portable computing device 200 can generate the input control waveforms and distribute the input control waveforms for the particular model of device (but generally not the particular device) preloaded with the portable computing device 200 in the input control waveform storage 216. As the sound of the input control 208 changes over time, for example as a spring in the input control 208 loses elasticity or parts in the input control 208 become worn, the noise cancellation module 214 can periodically or at predetermined times re-record and recalculate the input control waveforms. In some implementations, the noise cancellation module 214 can record the input control waveforms in the background while the portable computing device 200 performs another task. For example, the noise cancellation module 214 can record input control waveforms and associate the waveforms with corresponding activation events while the user types a document into a word processor application.

In some implementations, one or more of the noise cancellation module 214 and the input control waveform storage 216 can be included in a server system. For example, where processor power and/or storage capacity may be limited in the portable computing device 200, the server system can perform the noise cancellation operations of the noise cancellation module 214 and/or the storage of the input control waveform storage 216. In another example, the server system can perform the noise cancellation and storage functions if the server system is already being used as a proxy for the teleconference between the computing devices. In another example, the server system can perform the noise cancellation and storage functions if the modified audio is not needed for playback at the portable computing device 200 where it was first recorded and is only or primarily being sent to other computing devices.

Where a server system performs alteration of an audio signal, the sound model for providing cancellation may be specific to a particular user's device (and the model may be accessed in association with an account for the user) or may be more general and aimed at a particular make, class, or model of device. A user's account may store information that reflects such a device identifier, or data that identifies the type of device may be sent with the audio data and other data that is provided from the device to the server. The server may then use the identifying information to select the appropriate sound model for that device type from among multiple such sound models that the server system may store.

Returning to the particular components themselves, the noise cancellation module 214 passes the modified audio signal 218 to another application, device, or system, such as a teleconference application 220, the operating system of the portable computing device 200, or to another computing system or audio recording system. For example, the portable computing device 200 may be a portable or handheld video game device. The video game device receives the sound input 202 and cancels the sounds of one or more input controls. The video game device can execute a video game which communicates with other video game consoles. Users can interact with the video game devices using input controls and speak to the users of the other video game devices with microphones. The video game or video game device can include the noise cancellation module 214 to modify user speech input by minimizing the sounds of activating the input controls that are picked up by the microphone 206.

In some implementations, the noise cancellation module 214 and/or the input control waveform storage 216 are included in a video game server system. The video game server system can store input control waveforms that are averaged over multiple ones of the video game devices and/or waveforms that are specific to individual video game devices. The video game devices can send unmodified speech inputs and information describing activation events occurring at the respective video game devices to the video game server system. The video game server system performs the noise cancellation on the speech inputs and forwards the modified speech inputs to the video game devices. In some implementations, the video game server system can add multiple speech inputs together to make a single modified audio signal that is then forwarded to the video game devices. In some implementations, the video game server system creates a single modified audio signal for each of the video game devices, such that the single modified audio signal sent to a particular video game device does not include the speech input that originated from that particular video game device.

In another example, the portable computing device 200 may be a mixing board that can receive an audio input, including a performer singing, and cancel noises from input controls on an instrument, such as from keys on an electronic keyboard or buttons on an electronic drum set. The mixing board receives the sound input 202 from the microphone 206, which includes the singing from the performer as well as the noise of mechanical manipulation of the electronic instrument (e.g., the noise of a pressed keyboard key or the noise of an electronic drumhead or button being struck or pressed). The mixing board includes the noise cancellation module 214 that detects activation events from the electronic instrument and filters the sound input 202 to remove or minimize the noise of the instrument in the audio input.

Figure 3:
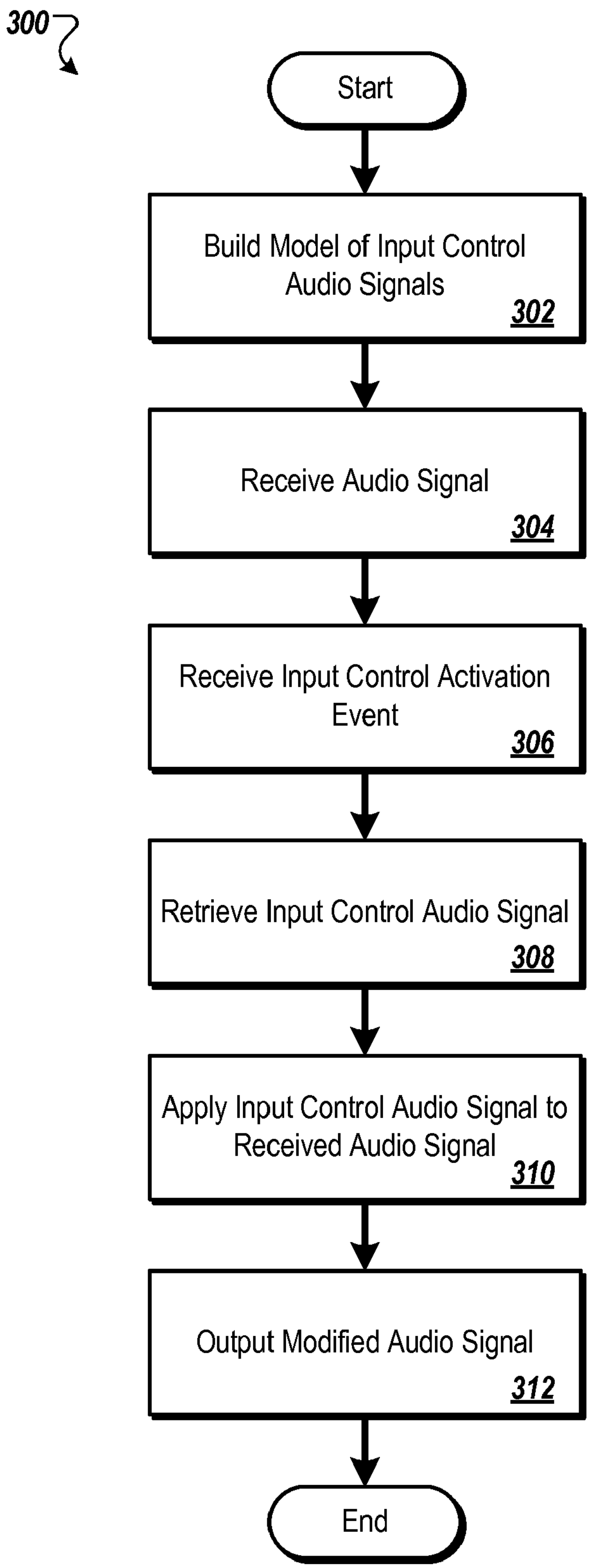
FIG. 3 is a flow chart that shows an example of a process for removing noise from audio.

FIG. 3 is a flow chart that shows an example of a process 300 for removing noise from audio. The process 300 may be performed, for example, by a system such as the system 100 or the portable computing device 200. For clarity of presentation, the description that follows uses the system 100 and the portable computing device 200 as examples for describing the process 300. However, another system, or combination of systems, may be used to perform the process 300.

Prior to an audio recording session, the process 300 begins with the building (302) of a model of input control audio signals that represent sound that is produced by activating one or more input controls. Such a phase may serve to help train the device. In addition, the input control audio signals are associated with corresponding input control activation events that result from activating the input controls. For example, the user 106 may initiate a calibration routine on the computing device 102. The computing device 102 can prompt the user to activate each of the input controls 110. The computing device 102 can then record and store the noises 112 associated with the activation of the input controls 110. Alternatively, the training process may place a paragraph or other block of text on a screen, and may ask the user to type the text in a quiet room, while correlating particular key presses (as sensed by activation of the keys) with observed sounds. Such observed sounds may, individually, be used as the basis for canceling signals that are applied later when their particular corresponding key is activated by a user.

During the audio recording session, the process 300 receives (304) a recording session audio signal recorded from a microphone in the computing device. For example, a user may speak into the microphone 206, and the microphone 206 can generate the audio signal 210.

Also during the audio recording session, the process 300 receives (306) an input control activation event that results from activation of a corresponding one of the input controls. The received input control activation event is included among the input control activation events associated with the input control audio signals. For example, the user may also activate the input controls 208, which can generate the activation event 212.

The process 300 retrieves (308) an input control audio signal that is associated with the received input control activation event from among the input control audio signals in the model. For example, the noise cancellation module 214 can retrieve the input control audio signal from the input control waveform storage 216 that is associated with the activation event 212.

The process 300 applies (310) the input control audio signal to the received recording session audio signal to remove the input control audio signal from the received recording session audio signal. For example, the noise cancellation module 214 can receive the activation event 212 and look up an input control audio signal from the input control waveform storage 216. The noise cancellation module 214, after delaying for a time difference associated with the input control audio signal and the activation event 212, applies the input control audio signal to the audio signal 210 to generate the modified audio signal 218.

The process 300 outputs (312) the modified audio signal through an audio interface of the computing device or through a network interface to another computing device or a computing system. For example, the noise cancellation module 214 can send the modified audio signal 218 to the teleconference application 220.

Figure 4:
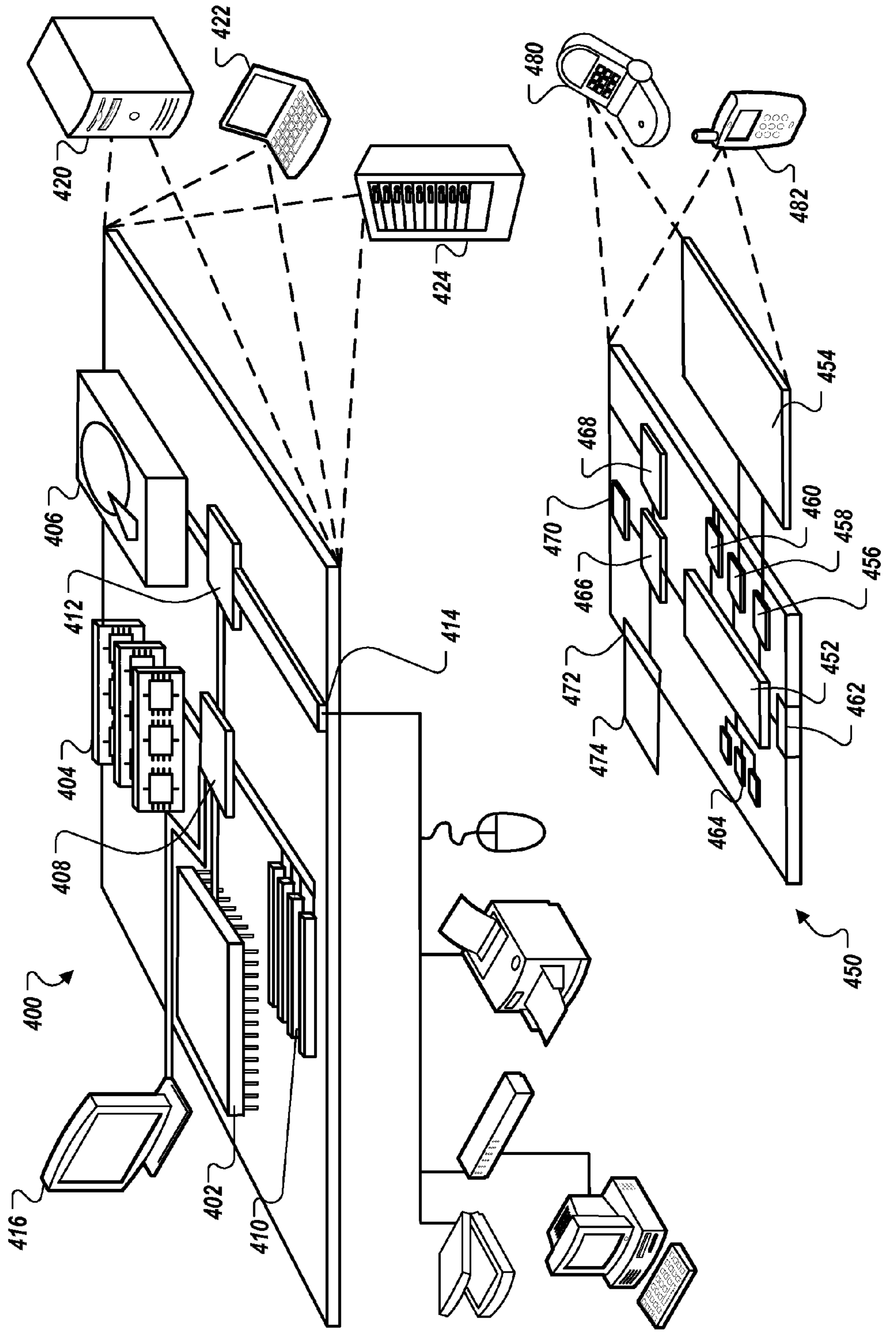
FIG. 4 shows an example of a computing device and a mobile computing device that can be used in connection with computer-implemented methods and systems described in this document.

FIG. 4 shows an example of a computing device 400 and a mobile computing device that can be used to implement the techniques described here. The computing device 400 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 400 includes a processor 402, a memory 404, a storage device 406, a high-speed interface 408 connecting to the memory 404 and multiple high-speed expansion ports 410, and a low-speed interface 412 connecting to a low-speed expansion port 414 and the storage device 406. Each of the processor 402, the memory 404, the storage device 406, the high-speed interface 408, the high-speed expansion ports 410, and the low-speed interface 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as a display 416 coupled to the high-speed interface 408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 404 stores information within the computing device 400. In some implementations, the memory 404 is a volatile memory unit or units. In some implementations, the memory 404 is a non-volatile memory unit or units. The memory 404 may also be another form of computer-readable medium, such as a magnetic or optical disk.

The storage device 406 is capable of providing mass storage for the computing device 400. In some implementations, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The computer program product can also be tangibly embodied in a computer- or machine-readable medium, such as the memory 404, the storage device 406, or memory on the processor 402.

The high-speed interface 408 manages bandwidth-intensive operations for the computing device 400, while the low-speed interface 412 manages lower bandwidth-intensive operations. Such allocation of functions is exemplary only. In some implementations, the high-speed interface 408 is coupled to the memory 404, the display 416 (e.g., through a graphics processor or accelerator), and to the high-speed expansion ports 410, which may accept various expansion cards (not shown). In the implementation, the low-speed interface 412 is coupled to the storage device 406 and the low-speed expansion port 414. The low-speed expansion port 414, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. In addition, it may be implemented in a personal computer such as a laptop computer 422. It may also be implemented as part of a rack server system 424. Alternatively, components from the computing device 400 may be combined with other components in a mobile device (not shown), such as a mobile computing device 450. Each of such devices may contain one or more of the computing device 400 and the mobile computing device 450, and an entire system may be made up of multiple computing devices communicating with each other.

The mobile computing device 450 includes a processor 452, a memory 464, an input/output device such as a display 454, a communication interface 466, and a transceiver 468, among other components. The mobile computing device 450 may also be provided with a storage device, such as a micro-drive or other device, to provide additional storage. Each of the processor 452, the memory 464, the display 454, the communication interface 466, and the transceiver 468, are interconnected using various buses, and several of the components may be mounted on a common motherboard or in other manners as appropriate.

The processor 452 can execute instructions within the mobile computing device 450, including instructions stored in the memory 464. The processor 452 may be implemented as a chipset of chips that include separate and multiple analog and digital processors. The processor 452 may provide, for example, for coordination of the other components of the mobile computing device 450, such as control of user interfaces, applications run by the mobile computing device 450, and wireless communication by the mobile computing device 450.

The processor 452 may communicate with a user through a control interface 458 and a display interface 456 coupled to the display 454. The display 454 may be, for example, a TFT (Thin-Film-Transistor Liquid Crystal Display) display or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may provide communication with the processor 452, so as to enable near area communication of the mobile computing device 450 with other devices. The external interface 462 may provide, for example, for wired communication in some implementations, or for wireless communication in other implementations, and multiple interfaces may also be used.

The memory 464 stores information within the mobile computing device 450. The memory 464 can be implemented as one or more of a computer-readable medium or media, a volatile memory unit or units, or a non-volatile memory unit or units. An expansion memory 474 may also be provided and connected to the mobile computing device 450 through an expansion interface 472, which may include, for example, a SIMM (Single In Line Memory Module) card interface. The expansion memory 474 may provide extra storage space for the mobile computing device 450, or may also store applications or other information for the mobile computing device 450. Specifically, the expansion memory 474 may include instructions to carry out or supplement the processes described above, and may include secure information also. Thus, for example, the expansion memory 474 may be provide as a security module for the mobile computing device 450, and may be programmed with instructions that permit secure use of the mobile computing device 450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 464, the expansion memory 474, or memory on the processor 452. In some implementations, the computer program product can be received in a propagated signal, for example, over the transceiver 468 or the external interface 462.

The mobile computing device 450 may communicate wirelessly through the communication interface 466, which may include digital signal processing circuitry where necessary. The communication interface 466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 468 using a radio-frequency. In addition, short-range communication may occur, such as using a Bluetooth, WiFi, or other such transceiver (not shown). In addition, a GPS (Global Positioning System) receiver module 470 may provide additional navigation- and location-related wireless data to the mobile computing device 450, which may be used as appropriate by applications running on the mobile computing device 450.

The mobile computing device 450 may also communicate audibly using an audio codec 460, which may receive spoken information from a user and convert it to usable digital information. The audio codec 460 may likewise generate audible sound for a user, such as through a speaker, e.g., in a handset of the mobile computing device 450. Such sound may include sound from voice telephone calls, may include recorded sound (e.g., voice messages, music files, etc.) and may also include sound generated by applications operating on the mobile computing device 450.

The mobile computing device 450 may be implemented in a number of different forms, as shown in the figure. For example, it may be implemented as a cellular telephone 480. It may also be implemented as part of a smart-phone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Although a few implementations have been described in detail above, other modifications are possible. For example, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A computer-implemented method for filtering noise from audio, the method comprising:

receiving, by a computing system, a first signal that encodes first audio obtained by a microphone of a first computing device that is different than the computing system;

selecting, by the computing system, a first sound model that corresponds to a first input control of the first computing device, the first sound model selected from among multiple sound models that correspond to multiple respective input controls, wherein the selected first sound model was generated by aggregating multiple signals that encode audio that resulted from multiple different respective activations of the first input control;

applying, by the computing system, the selected first sound model to the first signal that encodes the first audio, in order to filter, from the first signal, audio of user activation with the first input control so as to generate a first filtered signal;

providing, by the computing system, the first filtered signal to the first computing device for output by a speaker of the first computing device;

receiving, by the computing system, a second signal that encodes second audio obtained by a microphone of a second computing device that is different than the computing system and the first computing device;

selecting, by the computing system, a second sound model that corresponds to a second input control of the second computing device, the second sound model selected from among the multiple sound models; and applying, by the computing system, the selected second sound model to the second signal that encodes the second audio, in order to filter, from the second signal, audio of user activation with the second input control so as to generate a second filtered signal.

2. The computer-implemented method of claim 1, further comprising:

providing, by the computing system, the first filtered signal to a third computing device for output by a speaker of the third computing device, the third computing device being different than the computing system and the first computing device.

3. The computer-implemented method of claim 1, further comprising generating, by the computing system, the selected first sound model by averaging multiple waveforms that correspond to activation of the first input control at multiple different respective computing devices that are different than the computing system.

4. The computer-implemented method of claim 1, further comprising:

adding, by the computing system, the first filtered signal to other filtered signals so as to generate a single filtered signal, the other filtered signals having been generated by the computing system by applying particular ones of the multiple sound models to multiple different respective received signals that encode audio obtained by microphones of multiple different respective computing devices that are different than the computing system; and forwarding the single filtered signal for receipt by a particular computing device that is different than the computing system.

5. The computer-implemented method of claim 1, further comprising periodically recalculating, by the computing system, the selected first sound model that corresponds to the first input control.

6. The computer-implemented method of claim 1, wherein the first audio was obtained by the microphone of the first computing device while a user of the first computing device typed content into a word processor application.

7. The computer-implemented method of claim 1, further comprising receiving, by the computing system, a first indication of user activation with the first input control.

8. A computer-implemented method for filtering noise from audio, the method comprising:

receiving, by a computing system, a first signal that encodes first audio obtained by a microphone of a first computing device that is different than the computing system;

receiving, by the computing system, an indication of a type of the first computing device;

selecting, by the computing system, a first sound model that corresponds to a first input control of the first computing device, the first sound model selected from among multiple sound models that correspond to multiple respective input controls, wherein the selected first sound model is selected to be specific to the type of the first computing device, and at least a plurality of the multiple sound models are specific to multiple different respective types of computing devices that are different than the computing system;

applying, by the computing system, the selected first sound model to the first signal that encodes the first audio, in order to filter, from the first signal, audio of user activation with the first input control so as to generate a first filtered signal;

receiving, by the computing system, a second signal that encodes second audio obtained by a microphone of a second computing device that is different than the computing system and the first computing device;

selecting, by the computing system, a second sound model that corresponds to a second input control of the second computing device, the second sound model selected from among the multiple sound models; and applying, by the computing system, the selected second sound model to the second signal that encodes the second audio, in order to filter, from the second signal, audio of user activation with the second input control so as to generate a second filtered signal.

9. A computer-implemented method for filtering noise from audio, the method comprising:

receiving, by a computing system, a first signal that encodes first audio obtained by a microphone of a first computing device that is different than the computing system;

selecting, by the computing system, a first sound model that corresponds to a first input control of the first computing device, the first sound model selected from among multiple sound models that correspond to multiple respective input controls, wherein the selected first sound model was generated as a result of a training process in which a block of text was displayed on a screen and a user was prompted to type the block of text;

applying, by the computing system, the selected first sound model to the first signal that encodes the first audio, in order to filter, from the first signal, audio of user activation with the first input control so as to generate a first filtered signal;

receiving, by the computing system, a second signal that encodes second audio obtained by a microphone of a second computing device that is different than the computing system and the first computing device;

selecting, by the computing system, a second sound model that corresponds to a second input control of the second computing device, the second sound model selected from among the multiple sound models; and applying, by the computing system, the selected second sound model to the second signal that encodes the second audio, in order to filter, from the second signal, audio of user activation with the second input control so as to generate a second filtered signal.

10. A computer-implemented method for filtering noise from audio, the method comprising:

receiving, by a computing system, a first signal that encodes first audio obtained by a microphone of a first computing device that is different than the computing system;

receiving, by the computing system, a first indication of user activation with a first input control;

receiving, by the computing system, a first indication of a time that the user activation with the first input control occurred relative to the first signal that encodes the first audio;

selecting, by the computing system, a first sound model that corresponds to the first input control of the first computing device, the first sound model selected from among multiple sound models that correspond to multiple respective input controls;

applying, by the computing system, the selected first sound model to the first signal that encodes the first audio, in order to filter, from the first signal, audio of user activation with the first input control so as to generate a first filtered signal;

receiving, by the computing system, a second signal that encodes second audio obtained by a microphone of a second computing device that is different than the computing system and the first computing device;

selecting, by the computing system, a second sound model that corresponds to a second input control of the second computing device, the second sound model selected from among the multiple sound models; and applying, by the computing system, the selected second sound model to the second signal that encodes the second audio, in order to filter, from the second signal, audio of user activation with the second input control so as to generate a second filtered signal.

11. The computer-implemented method of claim 10, wherein the indication of the time includes an indication of an amount of time between (a) the first computing device identifying the user activation with the first input control and (b) the first computing device encoding the first audio in the first signal.

12. A computer-implemented method, the method comprising:

receiving, by a computing system, multiple signals that encode audio obtained by microphones of multiple respective computing devices that are different than the computing system and that represent sounds generated by user activations of a type of input control at the multiple respective computing devices;

generating, by the computing system, a sound model by combining the multiple signals that represent the sounds generated by the user activations of the type of input control at the multiple respective computing devices; and storing the sound model for application to a particular signal that encodes audio, in order to filter, from the particular signal, audio of a user activation of the type of input control.

13. The computer-implemented method of claim 12, further comprising:

receiving, by the computing system, the particular signal that encodes the audio from a particular computing device that is different than the computing system, the audio having been obtained by a microphone of the particular computing device, the particular signal representing sound generated by user activation of the type of input control at the particular computing device; and applying, by the computing system, the stored sound model to the particular signal to filter, from the particular signal, audio of user activation with the type of input control so as to generate a filtered signal.

14. The computer-implemented method of claim 13, further comprising providing the filtered signal to the particular computing device.

15. The computer-implemented method of claim 12, wherein combining the multiple signals comprises averaging the multiple signals.

16. A computer-implemented method for filtering noise from audio, the method comprising:

receiving, by a computing system, a first signal that encodes first audio obtained by a microphone of a first computing device that is different than the computing system;

selecting, by the computing system, a first sound model that corresponds to a first input control of the first computing device, the first sound model selected from among multiple sound models that correspond to multiple respective input controls, wherein the selected first sound model was generated by aggregating multiple waveforms that correspond to activation of the first input control at multiple different respective computing devices that are different than the computing system;

applying, by the computing system, the selected first sound model to the first signal that encodes the first audio, in order to filter, from the first signal, audio of user activation with the first input control so as to generate a first filtered signal;

receiving, by the computing system, a second signal that encodes second audio obtained by a microphone of a second computing device that is different than the computing system and the first computing device;

selecting, by the computing system, a second sound model that corresponds to a second input control of the second computing device, the second sound model selected from among the multiple sound models; and applying, by the computing system, the selected second sound model to the second signal that encodes the second audio, in order to filter, from the second signal, audio of user activation with the second input control so as to generate a second filtered signal.

17. A system, comprising:

a processor; and a computer-readable device including instructions that, when executed by the processor, cause performance of a method that comprises:

receiving, by a computing system, a first signal that encodes first audio obtained by a microphone of a first computing device that is different than the computing system;

selecting, by the computing system, a first sound model that corresponds to a first input control of the first computing device, the first sound model selected from among multiple sound models that correspond to multiple respective input controls, wherein the selected first sound model was generated by aggregating multiple signals that encode audio that resulted from multiple different respective activations of the first input control;

applying, by the computing system, the selected first sound model to the first signal that encodes the first audio, in order to filter, from the first signal, audio of user activation with the first input control so as to generate a first filtered signal;

providing, by the computing system, the first filtered signal to the first computing device for output by a speaker of the first computing device;

receiving, by the computing system, a second signal that encodes second audio obtained by a microphone of a second computing device that is different than the computing system and the first computing device;

selecting, by the computing system, a second sound model that corresponds to a second input control of the second computing device, the second sound model selected from among the multiple sound models; and applying, by the computing system, the selected second sound model to the second signal that encodes the second audio, in order to filter, from the second signal, audio of user activation with the second input control so as to generate a second filtered signal.

18. The system of claim 17, wherein the method further comprises:

providing, by the computing system, the first filtered signal to a third computing device for output by a speaker of the third computing device, the third computing device being different than the computing system and the first computing device.

19. The system of claim 17, wherein the method further comprises:

generating, by the computing system, the selected first sound model by averaging multiple waveforms that correspond to activation of the first input control at multiple different respective computing devices that are different than the computing system.

20. The system of claim 17, wherein the method further comprises:

adding, by the computing system, the first filtered signal to other filtered signals so as to generate a single filtered signal, the other filtered signals having been generated by the computing system by applying particular ones of the multiple sound models to multiple different respective received signals that encode audio obtained by microphones of multiple different respective computing devices that are different than the computing system; and forwarding the single filtered signal for receipt by a particular computing device that is different than the computing system.

21. The system of claim 17, wherein the method further comprises:

periodically recalculating, by the computing system, the selected first sound model that corresponds to the first input control.

22. The system of claim 17, wherein the first audio was obtained by the microphone of the first computing device while a user of the first computing device typed content into a word processor application.

23. The system of claim 17, wherein the method further comprises:

receiving, by the computing system, a first indication of user activation with the first input control.

24. A system, comprising:

a processor; and a computer-readable device including instructions that, when executed by the processor, cause performance of a method that comprises:

receiving, by a computing system, a first signal that encodes first audio obtained by a microphone of a first computing device that is different than the computing system;

receiving, by the computing system, an indication of a type of the first computing device;

selecting, by the computing system, a first sound model that corresponds to a first input control of the first computing device, the first sound model selected from among multiple sound models that correspond to multiple respective input controls, wherein the selected first sound model is selected to be specific to the type of the first computing device, and at least a plurality of the multiple sound models are specific to multiple different respective types of computing devices that are different than the computing system;

applying, by the computing system, the selected first sound model to the first signal that encodes the first audio, in order to filter, from the first signal, audio of user activation with the first input control so as to generate a first filtered signal;

receiving, by the computing system, a second signal that encodes second audio obtained by a microphone of a second computing device that is different than the computing system and the first computing device;

selecting, by the computing system, a second sound model that corresponds to a second input control of the second computing device, the second sound model selected from among the multiple sound models; and applying, by the computing system, the selected second sound model to the second signal that encodes the second audio, in order to filter, from the second signal, audio of user activation with the second input control so as to generate a second filtered signal.

25. A system, comprising:

a processor; and a computer-readable device including instructions that, when executed by the processor, cause performance of a method that comprises:

receiving, by a computing system, a first signal that encodes first audio obtained by a microphone of a first computing device that is different than the computing system;

selecting, by the computing system, a first sound model that corresponds to a first input control of the first computing device, the first sound model selected from among multiple sound models that correspond to multiple respective input controls, wherein the selected first sound model was generated as a result of a training process in which a block of text was displayed on a screen and a user was prompted to type the block of text;

applying, by the computing system, the selected first sound model to the first signal that encodes the first audio, in order to filter, from the first signal, audio of user activation with the first input control so as to generate a first filtered signal;

receiving, by the computing system, a second signal that encodes second audio obtained by a microphone of a second computing device that is different than the computing system and the first computing device;

selecting, by the computing system, a second sound model that corresponds to a second input control of the second computing device, the second sound model selected from among the multiple sound models; and applying, by the computing system, the selected second sound model to the second signal that encodes the second audio, in order to filter, from the second signal, audio of user activation with the second input control so as to generate a second filtered signal.

26. A system, comprising:

a processor; and a computer-readable device including instructions that, when executed by the processor, cause performance of a method that comprises:

receiving, by a computing system, a first signal that encodes first audio obtained by a microphone of a first computing device that is different than the computing system;

receiving, by the computing system, a first indication of user activation with a first input control;

receiving, by the computing system, a first indication of a time that the user activation with the first input control occurred relative to the first signal that encodes the first audio;

selecting, by the computing system, a first sound model that corresponds to the first input control of the first computing device, the first sound model selected from among multiple sound models that correspond to multiple respective input controls;

applying, by the computing system, the selected first sound model to the first signal that encodes the first audio, in order to filter, from the first signal, audio of user activation with the first input control so as to generate a first filtered signal;

receiving, by the computing system, a second signal that encodes second audio obtained by a microphone of a second computing device that is different than the computing system and the first computing device;

selecting, by the computing system, a second sound model that corresponds to a second input control of the second computing device, the second sound model selected from among the multiple sound models; and applying, by the computing system, the selected second sound model to the second signal that encodes the second audio, in order to filter, from the second signal, audio of user activation with the second input control so as to generate a second filtered signal.

27. The system of claim 26, wherein the indication of the time includes an indication of an amount of time between (a) the first computing device identifying the user activation with the first input control and (b) the first computing device encoding the first audio in the first signal.

28. A system, comprising:

a processor; and a computer-readable device including instructions that, when executed by the processor, cause performance of a method that comprises:

receiving, by a computing system, multiple signals that encode audio obtained by microphones of multiple respective computing devices that are different than the computing system and that represent sounds generated by user activations of a type of input control at the multiple respective computing devices;

generating, by the computing system, a sound model by combining the multiple signals that represent the sounds generated by the user activations of the type of input control at the multiple respective computing devices; and storing the sound model for application to a particular signal that encodes audio, in order to filter, from the particular signal, audio of a user activation of the type of input control.

29. The system of claim 28, wherein the method further comprises:

receiving, by the computing system, the particular signal that encodes the audio from a particular computing device that is different than the computing system, the audio having been obtained by a microphone of the particular computing device, the particular signal representing sound generated by user activation of the type of input control at the particular computing device; and applying, by the computing system, the stored sound model to the particular signal to filter, from the particular signal, audio of user activation with the type of input control so as to generate a filtered signal.

30. The system of claim 29, wherein the method further comprises providing the filtered signal to the particular computing device.

31. The system of claim 28, wherein combining the multiple signals comprises averaging the multiple signals.

32. A system, comprising:

a processor; and a computer-readable device including instructions that, when executed by the processor, cause performance of a method that comprises:

receiving, by a computing system, a first signal that encodes first audio obtained by a microphone of a first computing device that is different than the computing system;

selecting, by the computing system, a first sound model that corresponds to a first input control of the first computing device, the first sound model selected from among multiple sound models that correspond to multiple respective input controls, wherein the selected first sound model was generated by aggregating multiple waveforms that correspond to activation of the first input control at multiple different respective computing devices that are different than the computing system;

applying, by the computing system, the selected first sound model to the first signal that encodes the first audio, in order to filter, from the first signal, audio of user activation with the first input control so as to generate a first filtered signal;

receiving, by the computing system, a second signal that encodes second audio obtained by a microphone of a second computing device that is different than the computing system and the first computing device;

selecting, by the computing system, a second sound model that corresponds to a second input control of the second computing device, the second sound model selected from among the multiple sound models; and applying, by the computing system, the selected second sound model to the second signal that encodes the second audio, in order to filter, from the second signal, audio of user activation with the second input control so as to generate a second filtered signal.

* * * * *